US008540720B2

(12) United States Patent
Garcia-Bengochea et al.

(10) Patent No.: US 8,540,720 B2
(45) Date of Patent: Sep. 24, 2013

(54) SYSTEM, INSTRUMENTATION AND METHOD FOR SPINAL FIXATION USING MINIMALLY INVASIVE SURGICAL TECHNIQUES

(76) Inventors: Javier Garcia-Bengochea, Jacksonville, FL (US); Andrew F. Cannestra, Jacksonville, FL (US)

( * ) Notice: Subject to any disclaimer, the term of this patent is extended or adjusted under 35 U.S.C. 154(b) by 8 days.

(21) Appl. No.: 12/931,953

(22) Filed: Feb. 14, 2011

(65) Prior Publication Data
US 2011/0184475 A1    Jul. 28, 2011

Related U.S. Application Data

(63) Continuation-in-part of application No. 12/315,546, filed on Dec. 4, 2008.

(60) Provisional application No. 61/005,523, filed on Dec. 6, 2007.

(51) Int. Cl.
*A61B 17/70* (2006.01)

(52) U.S. Cl.
USPC ...................................... 606/86 A

(58) Field of Classification Search
USPC ........ 606/246, 279, 86 A, 86 R, 99, 103–105; 600/201–235
See application file for complete search history.

(56) References Cited

U.S. PATENT DOCUMENTS

| | | | | |
|---|---|---|---|---|
| 6,821,277 B2 * | 11/2004 | Teitelbaum | ................ | 606/86 A |
| 7,056,321 B2 * | 6/2006 | Pagliuca et al. | ............ | 606/86 A |
| 7,179,261 B2 | 2/2007 | Sicvol et al. | | |
| 7,188,626 B2 | 3/2007 | Foley et al. | | |
| 7,250,052 B2 | 7/2007 | Landry et al. | | |
| 7,758,617 B2 * | 7/2010 | Iott et al. | ....................... | 606/246 |
| 8,038,699 B2 * | 10/2011 | Cohen et al. | .................. | 606/246 |
| 2002/0082598 A1 * | 6/2002 | Teitelbaum | .................... | 606/61 |
| 2005/0277934 A1 * | 12/2005 | Vardiman | ...................... | 606/61 |
| 2008/0015582 A1 * | 1/2008 | DiPoto et al. | .................. | 606/61 |
| 2008/0275458 A1 * | 11/2008 | Bleich et al. | ................. | 606/103 |
| 2009/0171391 A1 * | 7/2009 | Hutton et al. | ................. | 606/246 |
| 2010/0004701 A1 * | 1/2010 | Malandain et al. | ........ | 606/86 R |
| 2010/0087828 A1 * | 4/2010 | Krueger et al. | ................ | 606/93 |

* cited by examiner

*Primary Examiner* — Jan Christopher Merene
*Assistant Examiner* — Steven Cotroneo
(74) *Attorney, Agent, or Firm* — Thomas C. Saitta

(57) ABSTRACT

A cable threader device for passing a guide cable between pedicle screws during minimally invasive spinal surgery, the device comprising a handle with a trigger mechanism, the handle mounted onto an elongated shaft having a curved free end with a detachable curved lead member retained in telescoping manner on the end of the body. The guide cable is affixed to the lead member, the instrument is inserted into a first screw tower, the trigger mechanism is activated to advance the lead member into the adjacent tower, and the lead member and guide cable are retrieved through the second tower. Alternatively, the lead member is a hollow sleeve and the guide cable is pushed through the lead member.

6 Claims, 2 Drawing Sheets

SYSTEM, INSTRUMENTATION AND METHOD FOR SPINAL FIXATION USING MINIMALLY INVASIVE SURGICAL TECHNIQUES

This application is a continuation-in-part of U.S. patent application Ser. No. 12/315,546, filed Dec. 4, 2008, claiming the benefit of U.S. Provisional Patent Application Ser. No. 61/005,323, filed Dec. 4, 2007, the disclosures of both of which are incorporated herein by reference.

BACKGROUND OF THE INVENTION

This invention relates generally to the field of systems, instrumentation and methodology for the fixation of vertebrae relative to each other, and more particularly relates to such systems, instrumentation and methodology that utilize pedicle screws affixed to vertebral pedicles and one or more rods that rigidly join the pedicle screws of plural vertebrae. The invention contemplates the combination and use of plural pedicle screws, one or more rods and means to optimize insertion of the rod into the pedicle screws, such means comprising a guide cable and instrumentation to position the guide cable in the pedicle screws, whereby the screws are implanted into the vertebrae, the guide cable positioned in the screws and the rod subsequently guided into the pedicle screws along the guide cable, all using minimally invasive surgical incisions. With regard to instrumentation of the invention, the invention relates to guide cable threading or advancing devices adapted to pass the guide cable from one pedicle screw to an adjacent pedicle screw.

Early surgical techniques for affixing rods to vertebrae entailed relatively long incisions to provide access to the vertebrae. Newer techniques utilize multiple percutaneous stab incisions at chosen locations rather than a single long incision. Such techniques are often referred to as minimally invasive surgery (MIS). The MIS techniques are preferable with regard to recovery time.

One advanced MIS technique provides for the placement and passing of a guide cable or wire between the pedicle screws such that the guide cable can be utilized to direct and/or pull a fixation rod into proper position spanning the pedicle screws. Inserting and passing the guide cable through the tissue between the pedicle screws can be a difficult and time-consuming task. It is an object of this invention therefore to provide an instrument that greatly reduces the difficulty in this task.

SUMMARY OF THE INVENTION

The invention comprises in general an instrument and method of using the instrument in conjunction with the combination and use of plural pedicle screws implanted into vertebrae, screw extenders or towers extending from the pedicle screws to provide access to the heads of the screws, one or more rods for connecting the pedicle screws in a relatively rigid manner to prevent undesirable movement of the vertebrae, wherein a guide cable is inserted and positioned between the heads of the pedicle screws to guide the rod into proper position bridging the pedicle screws, all using minimally invasive surgical incisions. The instrument is a cable threader device, the device comprising a handle with a trigger mechanism, the handle mounted onto an elongated shaft having a curved free end with a detachable curved lead member retained in telescoping manner on the end of the shaft, the lead member having means to receive or connect the guide cable thereto. With this structure, the guide cable is attached to the lead member and the free end of the instrument is inserted into one of the screw towers facing the adjacent screw tower, such that when the trigger is actuated the lead member is extended to and into the adjacent screw tower, where the lead member can be grasped and pulled from the tower to advance the guide cable. The instrument is then removed form the first tower, the lead member is reattached to the elongated shaft and reinserted into the tower so as to face the next tower. The steps are repeated until the guide cable has been passed through all the pedicle screws.

In an alternative embodiment, the lead member is non-detachable from the free end and comprises a hollow sleeve open at both ends, such that when the lead member is advanced the combination of the curved free end and the lead member defines a tunnel though which the guide cable is pushed, the end of the guide cable or a loop of the guide cable if it is doubled back on itself then passing directly into the second pedicle screw tower, where it can be grasped and pulled out of the patient's body.

DETAILED DESCRIPTION OF THE INVENTION

Figure 1:
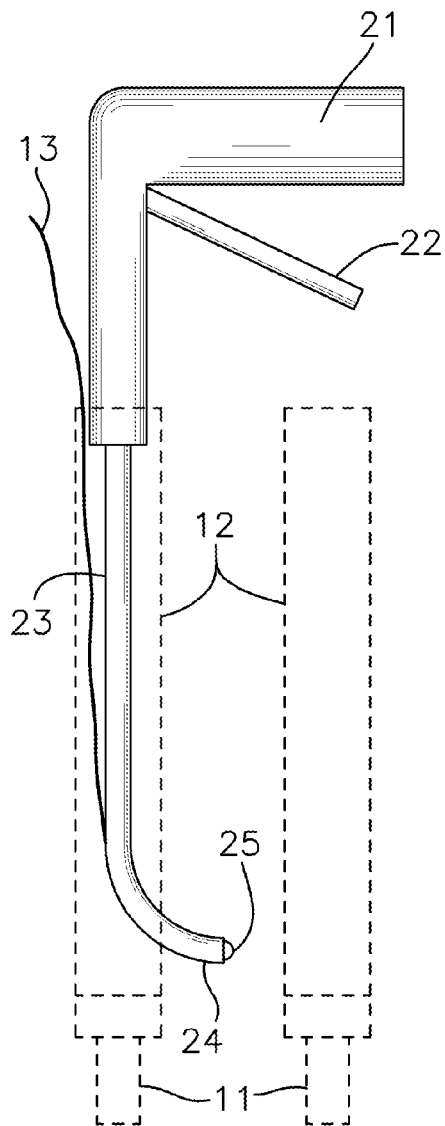
FIG. 1 illustrates a side view of the cable threader instrument showing the instrument inserted into a first screw tower.
Figure 2:
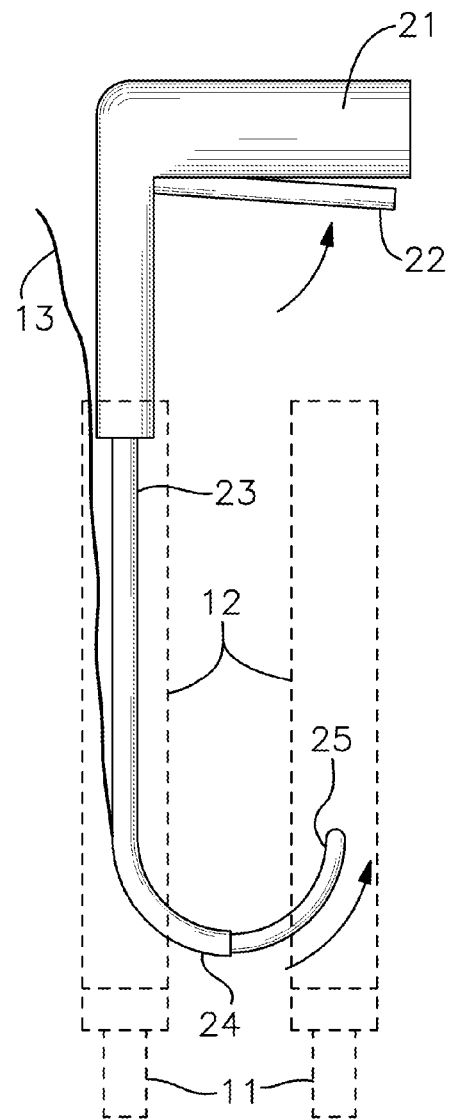
FIG. 2 is a side view similar to FIG. 1 showing the lead member advanced into an adjacent screw tower.
Figure 3:
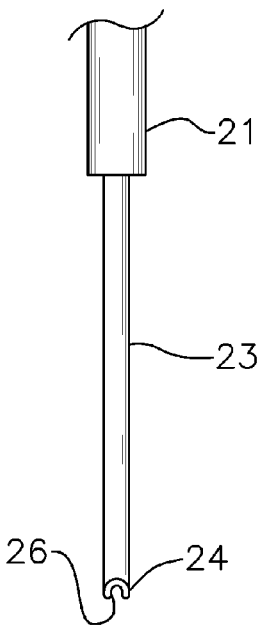
FIG. 3 is a front view of the instrument showing the guide cable receiving channel.
Figure 4:
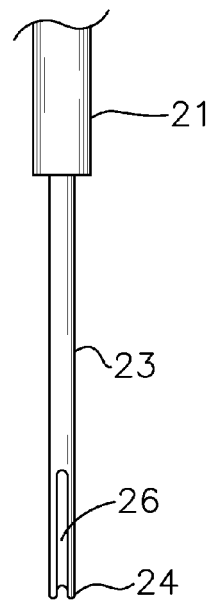
FIG. 4 is a rear view of the instrument showing the guide cable receiving channel
Figure 5:
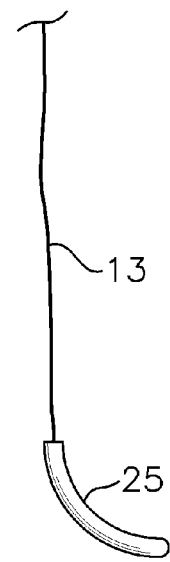
FIG. 5 is a side view showing the guide cable connected to the detachable lead member.

With reference to the drawings the invention will now be described in detail with regard for the best mode and the preferred embodiment. The invention comprises in general an instrument and method of using the instrument in conjunction with the combination and use of plural pedicle screws 11 implanted into vertebrae, screw extenders or towers 12 extending from the pedicle screws 11 to provide access to the heads of the screws 11, one or more rods for connecting the pedicle screws 11 in a relatively rigid manner to prevent undesirable movement of the vertebrae, wherein a guide cable or wire 13 is inserted and positioned between the heads of the pedicle screws 11 to guide the rod into proper position bridging the pedicle screws 11, all using minimally invasive surgical incisions.

Pedicle fixation is accomplished by creating multiple percutaneous incisions, as opposed to an open or long incision, often referred to as stab incisions. The percutaneous incisions allow for pedicle screws 11 to be inserted into each desired vertebra by cutting or making a short incision, drilling into the vertebra and inserting a pedicle screw 11. Screw extenders or towers 12 are connected to the pedicle screws 11 the towers 12 having slotted sides to provide access to their interiors. The guided cable 13, preferably a braided member composed of stainless steel or titanium, is either attached directly to the head of the first or outermost of the pedicle screws 11 or the free end is allowed to remain outside of the patient.

The instrument used to manipulate the guide cable 13 is a cable threader device, the device comprising a handle 21 with a trigger mechanism 22, the handle 21 mounted onto an elongated shaft 23 having a curved free end 24 with a detachable curved lead member 25 retained in telescoping manner on the end of the shaft 23, the lead member 25 having a rounded nose and means for connecting the guide cable 13 thereto, such as a hook or other mechanical fastening mechanism. Preferably the handle 21 and shaft 23 are rotatably joined. The combination of free end 24 and elongated shaft 23 define a general J-shape. The curved free end 24 of the instrument is provided with a cable slot 26 to temporarily receive the guide cable 13. With this structure, the guide cable 13 is attached to the lead member 25 and the free end 24 of the instrument is inserted into one of the screw towers 12 facing the adjacent screw tower 12, such that when the trigger mechanism 22 is actuated the lead member 25 is extended through the intervening tissue and into the adjacent screw tower 12, where the lead member 25 can be grasped using forceps or similar devices and pulled from the tower 12 to advance the guide cable 13. The trigger mechanism 22 may comprise any suitable known arrangement of elements, such as a relatively rigid cable or rod advanced downwardly in the shaft 23 by compression of the trigger mechanism 22. The instrument is then removed from the first tower 12, the intermediate portion of the guide wire 13 is separated from the instrument, and the lead member 25 is reattached to the elongated shaft 23 and reinserted into the tower 12 so as to face the next tower 12. The steps are repeated until the guide cable 13 has been passed through all the pedicle screws 11.

Figure 6:
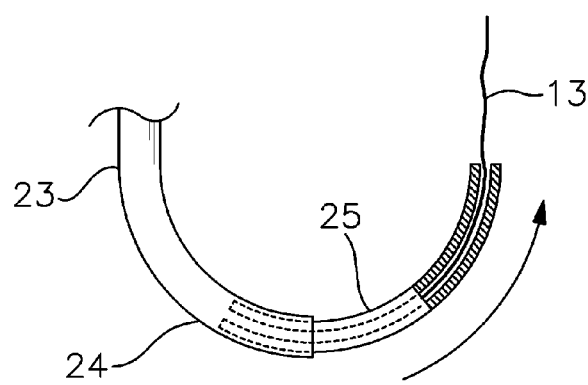
FIG. 6 is a side view showing an alternative embodiment of the lead member, shown partially in cross-section, wherein the lead member is a hollow sleeve.

In an alternate embodiment depicted in FIG. 6, the lead member 25 comprises a hollow sleeve open at both ends, such that when the lead member 25 is advanced the combination of the curved free end 24 and the lead member 25 defines a tunnel through which the guide cable 13 is pushed, the end of the guide cable 13 or a loop of the guide cable 13 if it is doubled back on itself then passing directly into the second pedicle screw tower 25, where it can be grasped and pulled out of the patient's body. The instrument is then removed from the first tower 25 and from the guide cable 13, and the free end or loop of the guide cable 13 extending from the second tower 25 is then reinserted into the instrument and the process is repeated.

Once the cable 13 has been properly positioned in the heads of the pedicle screws 11, it is finally brought out through a percutaneous incision at an offset or displaced location. A cannulated or tubular rod is then inserted over the free end of the cable 13 and passed down the cable 13 through the offset incision using a rod insertion instrument. The rod is preferably malleable in vivo to account for torque imparted by the set screws used to secure the rod to the pedicle screws 11. After the rod is properly positioned, the rod is affixed or secured to the pedicle screws 11 in standard manner, the cable 13 is cut or withdraw and the screw towers 12 are removed.

It is understood that equivalents and substitutions for elements set forth above may be obvious to those of ordinary skill in the art, and therefore the true scope and definition of the invention is to be as set forth in the following claims.

We claim:

1. A method of advancing a guide cable from a first pedicle screw tower to a second pedicle screw tower comprising the steps of:
    providing a guide cable threader device comprising a handle, a trigger mechanism disposed in said handle, an elongated shaft extending from said handle, said shaft having a curved free end, and a detachable curved lead member telescopically disposed in said free end of said elongated shaft, said lead member adapted to retain a guide cable, said lead member extendable from said free end of said elongated shaft upon actuation of said trigger mechanism;
    attaching a guide cable to said lead member and mounting said lead member to said free end of said shaft;
    inserting said shaft, said free end and said lead member into said first pedicle screw tower with said lead member facing said second pedicle screw tower;
    actuating said trigger mechanism to extend said lead member from said free end and into said second pedicle screw tower;
    grasping said lead member within said second pedicle tower, disconnecting said lead member from said free end, and pulling said lead member and said guide cable from said second pedicle screw tower;
    removing said shaft from said first pedicle screw tower; and
    re-attaching said lead member to said free end of said shaft.

2. The method of claim 1, wherein said free end of said elongated shaft comprises a cable slot, and wherein said step of mounting said lead member to said free end of said shaft further comprises positioning said guide cable within said cable slot;
    further comprising the step of removing said guide cable from said cable slot after said shaft is removed from said first pedicle screw tower.

3. The method of claim 2, wherein said step of positioning said guide cable within said cable slot further comprises positioning the remainder of said guide cable externally to said elongated shaft.

4. The method of claim 1, wherein said step of attaching a guide cable to said lead member comprises attaching said guide cable to the end of said lead member.

5. The method of claim 1, wherein said step of providing a guide cable threader device comprising a lead member further comprises providing a hollow lead member with open ends, and wherein said step of attaching a guide cable to said lead member comprises inserting said guide cable through said lead member.

6. The method of claim 1, further comprising the step of attaching said guide cable to the first pedicle tower.

* * * * *